United States Patent [19]
Ponsati Obiols et al.

[11] Patent Number: 5,670,677
[45] Date of Patent: Sep. 23, 1997

[54] PROCESS FOR THE PRODUCTION OF COLOR- AND ODOR-STABLE QUATERNIZED FATTY ACID TRIETHANOLAMINE ESTER SALTS

[75] Inventors: Oriol Ponsati Obiols, Barcelona; Joaquim Bigorra Llosas, Sabadell, both of Spain

[73] Assignee: Henkel Kommanditgesellschaft auf Aktien, Duesseldorf, Germany

[21] Appl. No.: 522,371

[22] PCT Filed: Mar. 9, 1994

[86] PCT No.: PCT/EP94/00716
§ 371 Date: Sep. 18, 1995
§ 102(e) Date: Sep. 18, 1995

[87] PCT Pub. No.: WO94/21596
PCT Pub. Date: Sep. 29, 1994

[30] Foreign Application Priority Data

Mar. 18, 1993 [DE] Germany .......................... 43 08 792.2

[51] Int. Cl.$^6$ .................................................. C07C 101/00
[52] U.S. Cl. .......................... 554/114; 554/108; 554/109; 554/110; 252/174.22; 252/541

[58] Field of Search ..................................... 554/114, 108, 554/109, 110; 252/541, 174.22

[56] References Cited

FOREIGN PATENT DOCUMENTS

| | | |
|---|---|---|
| 0498050 | 8/1992 | European Pat. Off. . |
| 0525271 | 3/1993 | European Pat. Off. . |
| 3815270 | 11/1988 | Germany . |
| 9101295 | 2/1991 | WIPO . |

*Primary Examiner*—Deborah D. Carr
*Attorney, Agent, or Firm*—Ernest G. Szoke; Wayne C. Jaeschke; Henry E. Millson, Jr.

[57] ABSTRACT

A process for the production of color- and odor-stable quaternized fatty acid triethanolamine ester salts comprising the steps of A) partially or fully esterifying triethanolamine with at least one fatty acid in the presence of hypophosphorous acid;

B) adding a peroxide compound and an alkali metal boranate to the esterification product from step A); and C) quaternizing the esterification product with an alkyl halide, a (di)alkyl sulfate or an alkylene oxide in the presence of a phenol derivative and a hydroxycarboxylic acid.

20 Claims, No Drawings

PROCESS FOR THE PRODUCTION OF COLOR- AND ODOR-STABLE QUATERNIZED FATTY ACID TRIETHANOLAMINE ESTER SALTS

This application is a 371 of PCT/EP94/00716 filed Mar. 9, 1994.

FIELD OF THE INVENTION

This invention relates to a process for the production of color- and odor-stable quaternized fatty acid triethanolamine ester salts, in which fatty acids are reacted with triethanolamine, the esterification products are treated with peroxide compounds and alkali metal boranates and the quaternization is carried out in the presence of selected stabilizers.

PRIOR ART

Quaternized fatty acid triethanolamine ester salts, so-called (ester quats), are cationic surfactants which are acquiring increasing significance by virtue of their excellent fabric-softening effect and their high ecotoxicological compatibility. The articles by O. Ponsati in C.R. CED Congress, Barcelona, 1992, page 167 and R. Puchta in C.R. CED Congress, Sitges, 1993, page 59, are cited as representative of the literature available on this subject.

The ester quats are normally produced in a two-stage process in which triethanolamine is first partly esterified with fatty acids and the reaction product is subsequently alkylated or quaternized with ethylene oxide. Hypophosphorous acid and sodium hypophosphite have proved to be optimal catalysts for the esterification step. However, during working up, particularly at relatively high temperatures, decomposition of the hypophosphorous acid or its salts can occur and small quantities of phosphines are formed, resulting in an adverse effect on the odor of the product. Another problem in the production of ester quats is that products light in color after production are not stable in storage and can darken to a considerable extent with time which limits their commercial usefulness.

Accordingly, the problem addressed by the present invention was to develop a process for the production of quaternized fatty acid triethanolamine ester salts which would be free from the disadvantages described above.

DESCRIPTION OF THE INVENTION

The present invention relates to a process for the production of color- and odor-stable quaternized fatty acid triethanolamine ester salts corresponding to formula (I):

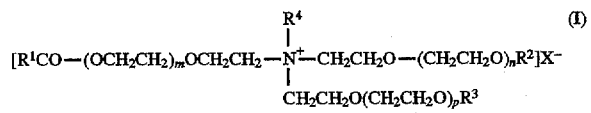

in which
R¹CO is an acyl radical containing 6 to 22 carbon atoms,
R² and R³ independently of one another represent hydrogen or have the same meaning as R¹CO,
R⁴ is an alkyl radical containing 1 to 4 carbon atoms or a (CH₂CH₂O)$_q$H group, q is a number from 1 to 12,
m, n and p together =0 or a number of 1 to 10 and
X is a halide, alkyl sulfate or alkyl phosphate,
in which
a) fatty acids are esterified with triethanolamine in the presence of hypophosphorous acid,
b) peroxide compounds and alkali metal boranates are added to the esterification products and
c) the quaternization is carried out in the presence of phenol derivatives and hydroxycarboxylic acids as stabilizers.

It has surprisingly been found that only the combination of features a), b) and c) leads to light-colored ester quats which are satisfactory in regard to odor and are stable in color, even in the event of prolonged storage. The invention includes the observation that, among the large number of known antioxidants, only selected substances are capable of stabilizing ester quats against color deterioration. Another significant observation is that even the proposed stabilizer system can only perform its function satisfactorily when it is added to the intermediate products, i.e. to the as yet unquaternized esters, and not to the end products.

Esterquats

Quaternized fatty acid triethanolamine ester salts are known substances which may obtained by the relevant methods of preparative organic chemistry. In this connection, reference is made to International patent application WO 91/01 295 (Henkel), according to which triethanolamine is partly esterified with fatty acids in the presence of hypophosphorous acid and, after has been passed through, the esterification product is subsequently quaternized with dimethyl sulfate or ethylene oxide.

The process according to the invention is preferably applied to ester quats which are produced using fatty acids corresponding to formula (II):

in which R¹CO is as defined above. Typical examples are caproic acid, caprylic acid. capric acid, lauric acid, myristic acid, palmitic acid, isostearic acid, stearic acid, oleic acid, elaidic acid, arachic acid, behenic acid and erucic acid and technical mixtures thereof such as are formed, for example, in the pressure hydrolysis of natural fats and oils. Technical C$_{12/18}$ coconut oil fatty acids and, in particular, partly hydrogenated C$_{16/18}$ tallow or palm oil fatty acids and C$_{16/18}$ fatty acid cuts rich in elaidic acid are preferably used.

To produce the quaternized esters, the fatty acids and the triethanolamine may be used in a molar ratio of 1.1:1 to 3:1. A ratio of 1.2:1 to 2.2:1, preferably 1.5:1 to 1.9:1, has proved to be particularly advantageous so far as the performance properties of the ester quats are concerned. The preferred esterquats are technical mixtures of mono-, di- and triesters with an average degree of esterification of 1.5 to 1.9 and are derived from technical C$_{16/18}$ tallow or palm oil fatty acid (iodine value 0 to 40).

Additives

In addition to percarboxylic acids and percarbonates, preferred peroxide compounds include hydrogen peroxide. Alkali metal boranates are understood to be lithium, potassium and, preferably, sodium boranate. The peroxide compounds and the alkali metal boranates are each advantageously used in quantities of 0.005 to 0.1% by weight and preferably in quantities of 0.03 to 0.06% by weight, based on the esterification products.

The stabilizers consist of two components. Suitable phenol derivatives are bis-alkyl hydroxytoluenes and/or bis-alkyl anisoles, more particularly 2,6-ditert. butyl-4-methyl toluene and 2,6-ditert. butyl anisole. Citric acid, tartaric acid and/or ascorbic acid, for example, may be used as the hydroxycarboxylic acids. The phenol derivatives and the hydroxycarboxylic acids are each advantageously used in quantities of 100 to 4000 ppm and preferably in quantities of 400 to 900 ppm, based on the quaternized ester. In one preferred embodiment of the process according to the invention, mixtures of 2,6-ditert. butyl-4-methyl phenol and citric acid are used as stabilizers.

The quaternization may be carried out in known manner with alkyl halides, (di)alkyl sulfates or alkylene oxides—the latter in the presence of (di)alkyl phosphates. The quaternization is preferably carried out with methyl chloride, dimethyl sulfate or ethylene oxide.

Commercial Applications

The quaternized fatty acid triethanolamine ester salts obtainable by the process according to the invention are light-colored, satisfactory in regard to odor and stable in storage. Accordingly, they are suitable for the production of laundry detergents, dishwashing detergents, cleaning products and fabric softeners and also for the production of hair-care and body-care products in which they may be present in quantities of 1 to 50% by weight and preferably 5 to 35% by weight, based on the particular product.

The following Examples are intended to illustrate the invention without limiting it in any way.

EXAMPLES

General procedure for the production of ester quats:

a) Esterification. 324 g (1.2 moles) of partly hydrogenated $C_{16/18}$ tallow fatty acid (iodine value 40), 149 g (1 mole) of triethanolamine and 0.5 g of 50% by weight hypophosphorous acid were introduced into a 1 liter three-necked flask equipped with a stirrer, internal thermometer and distillation column. The reaction mixture was heated to a temperature of 160° C. over a period of 4 h under a reduced pressure of 40 mbar until the acid value was below 5. The crude tallow fatty acid triethanolamine ester was then cooled and the reaction mixture was returned to normal pressure. First hydrogen peroxide and then sodium boranate were added to the ester at 60° C. After each addition, the mixture was stirred for 30 minutes. The stabilizer was then added.

b) Quaternization. A mixture of 450 g (1 mole) of the ester of b) in 200 ml of isopropyl alcohol was introduced into a 1 liter three-necked flask equipped with a stirrer, dropping funnel and reflux condenser and heated with stirring to 45° C. 119 g (0.95 mole) of dimethyl sulfate were then added dropwise over a period of 2 h. On completion of the addition, the mixture was stirred for another 2 h at 60° C. and unreacted DMS was destroyed by addition of 4 g (0.05 mole) of glycine. The solvent was then removed in a water jet vacuum. The yield of ester quat was 95% of the theoretical. Particulars of the test batches and the results obtained are set out in Table 1:

TABLE 1

Stabilization of ester quats
Percentages as % by weight

| Ex. | c(HP) % | c(SB) % | S1 | S2 | c(S1) ppm | c(S2) ppm | Color Klett |
|---|---|---|---|---|---|---|---|
| 1 | 0.05 | 0.01 | BHT | CA | 900 | 400 | 50 |
| 2 | 0.05 | 0.01 | DBA | CA | 900 | 400 | 75 |
| 3 | 0.05 | 0.01 | BHT | AA | 900 | 500 | 75 |
| C1 | — | 0.01 | BHT | CA | 900 | 400 | 200 |
| C2 | 0.05 | — | BHT | CA | 900 | 400 | 150 |
| C3 | 0.05 | 0.01 | — | — | — | — | 200 |
| C4 | 0.05 | 0.01 | BHT | — | 900 | — | 150 |
| C5 | 0.05 | 0.01 | — | CA | — | 400 | 150 |
| C6 | 0.05 | 0.01 | BHT | CA | 900 | 400 | 100* |

TABLE 1-continued

Stabilization of ester quats
Percentages as % by weight

| Ex. | c(HP) % | c(SB) % | S1 | S2 | c(S1) ppm | c(S2) ppm | Color Klett |
|---|---|---|---|---|---|---|---|
| C7 | 0.05 | 0.01 | BHT | TP | 900 | 400 | 150 |

Legend:
c(HP) = concentration of hydrogen peroxide
c(SR) = concentration of sodium boranate
c(S) = concentration of stabilizer
Color = measured in a Klett photometer, 5% active substance, 1 cm round cuvette after storage for 30 d (20° C.)
BHT = 2,6-ditert. butyl-4-methyl phenol
DBA = 2,6-ditert. butyl anisole
CA = citric acid
AA = ascorbic acid
TP = tocopherol
* = stabilizer added after the quaternization

We claim:

1. A process for the production of at least one color- and odor-stable quaternized fatty acid triethanolamine ester salt corresponding to formula (I):

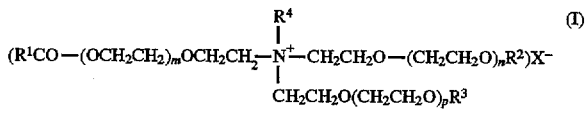

wherein
$R^1CO$ is an acyl radical containing 6 to 22 carbon atoms,
$R^2$ and $R^3$ independently of one another represent hydrogen or have the same meaning as $R^1CO$,
$R^4$ is an alkyl radical containing 1 to 4 carbon atoms or a $(CH_2CH_2O)_qH$ group, in which q is a number from 1 to 12,
m, n and p together=0 or a number of 1 to 10 and
X is a halide, alkyl sulfate or alkyl phosphate, comprising the steps of
A) partially or fully esterifying triethanolamine with at least one fatty acid of the formula $R^1COOH$ wherein $R^1CO$ is as defined above in the presence of hypophosphorous acid;
B) adding a peroxide compound and an alkali metal boranate to the esterification product from step A); and
C) quaternizing the esterification product with an alkyl halide, a (di)alkyl sulfate or an alkylene oxide in the presence of a phenol derivative and a hydroxycarboxylic acid, wherein where an alkylene oxide is used as the quaternizing agent, a (di)alkyl phosphate is also present.

2. The process of claim 1 wherein in step A) the molar ratio of fatty acid to triethanolamine is in the range of from about 1.1:1 to about 3:1.

3. The process of claim 2 wherein said molar ratio is from about 1.2:1 to about 2.2:1.

4. The process of claim 2 wherein said molar ratio is from about 1.5:1 to about 1.9:1.

5. The process of claim 1 wherein in step A) the at least one fatty acid is technical $C_{12/18}$ coconut oil fatty acids, partly hydrogenated $C_{16/18}$ tallow fatty acids, partly hydrogenated $C_{16/18}$ palm oil fatty acids, or a $C_{16/18}$ fatty acid mixture rich in elaidic acid.

6. The process of claim 1 wherein the at least one salt of formula I is a technical mixture of mono-, di-, and tri-esters having an average degree of esterification of from about 1.5 to about 1.9.

7. The process of claim 1 wherein in step B) the peroxide compound is added prior to the addition of the alkali metal boranate.

8. The process of claim 1 wherein in step B) hydrogen peroxide is used as the peroxide compound.

9. The process of claim 1 wherein in step B) sodium boranate is used as the alkali metal boranate.

10. The process of claim 7 wherein hydrogen peroxide is used as the peroxide compound and sodium boranate is used as the alkali metal boranate.

11. The process of claim 1 wherein in step B) the peroxide compound and the alkali metal boranate are each used in a quantity in the range of from about 0.005 to about 0.1% by weight, based on the esterification products.

12. The process of claim 11 wherein said quantity is in the range of from about 0.03 to about 0.06% by weight.

13. The process of claim 1 wherein in step C) the phenol derivative is at least one of a bis-alkyl hydroxytoluene and a bis-alkyl anisole.

14. The process of claim 13 wherein in step C) the hydroxycarboxylic acid is at least one of citric acid, tartaric acid, and ascorbic acid.

15. The process of claim 1 wherein in step C) the phenol derivative and the hydroxycarboxylic acid are each used in a quantity in the range of from about 100 to about 4000 ppm, based on the quaternized esterification product.

16. The process of claim 1 wherein in step C) the phenol derivative is 2, 6-ditert. butyl-4-methyl phenol and the hydroxycarboxylic acid is citric acid.

17. The process of claim 1 wherein in step C) the esterification product is quaternized with methyl chloride, dimethyl sulfate, or ethylene oxide.

18. In a laundry detergent, dishwashing detergent, cleaning product, fabric softener, hair-care product, or body-care product, the improvement wherein from about 1 to about 50% by weight of the at least one quaternized fatty acid triethanolamine ester salt of formula I produced by the process of claim 1 is present therein.

19. In a laundry detergent, dishwashing detergent, cleaning product, fabric softener, hair-care product, or body-care product, the improvement wherein from about 5 to about 35% by weight of the at least one quaternized fatty acid triethanolamine ester salt of formula I produced by the process of claim 1 is present therein.

20. In a laundry detergent, dishwashing detergent, cleaning product, fabric softener, hair-care product, or body-care product, the improvement wherein from about 1 to about 50% by weight of the at least one quaternized fatty acid triethanolamine ester salt of formula I produced by the process of claim 5 is present therein.

* * * * *